United States Patent [19]

Trolinder et al.

[11] Patent Number: 5,994,624
[45] Date of Patent: Nov. 30, 1999

[54] IN PLANTA METHOD FOR THE PRODUCTION OF TRANSGENIC PLANTS

[75] Inventors: Norma L. Trolinder; Linda Koonce, both of Lubbock, Tex.

[73] Assignee: Cotton Incorporated, New York, N.Y.

[21] Appl. No.: 08/953,987

[22] Filed: Oct. 20, 1997

[51] Int. Cl.$^6$ .......................... C12N 15/82; C12N 15/84; A01H 4/00
[52] U.S. Cl. ...................... 800/278; 435/252.2; 435/419; 435/172.3; 800/278; 800/314
[58] Field of Search .................... 435/252.2, 419, 435/172.3; 800/205, 250, DIG. 9, DIG. 27, DIG. 74, DIG. 52

[56] References Cited

U.S. PATENT DOCUMENTS

| | | | |
|---|---|---|---|
| 4,592,742 | 6/1986 | Landau | 604/71 |
| 4,849,355 | 7/1989 | Wong | 435/172.3 |
| 4,945,050 | 7/1990 | Sanford et al. | 435/172.1 |
| 4,966,581 | 10/1990 | Landau | 604/72 |
| 5,036,006 | 7/1991 | Sanford et al. | 435/170.1 |
| 5,098,843 | 3/1992 | Calvin | 435/287 |
| 5,120,657 | 6/1992 | McCabe et al. | 435/287 |
| 5,149,655 | 9/1992 | McCabe et al. | 435/287 |
| 5,159,135 | 10/1992 | Umbeck | 800/205 |
| 5,177,010 | 1/1993 | Goldman et al. | 435/172.3 |
| 5,179,022 | 1/1993 | Sanford et al. | 435/287 |
| 5,204,253 | 4/1993 | Sanford et al. | 435/172.3 |
| 5,240,842 | 8/1993 | Mets | 435/172.3 |
| 5,405,765 | 4/1995 | Vasil et al. | 435/172.3 |
| 5,521,078 | 5/1996 | John | 435/172.3 |
| 5,584,807 | 12/1996 | McCabe | 604/71 |
| 5,597,718 | 1/1997 | John et al. | 435/172.3 |
| 5,602,321 | 2/1997 | John | 800/205 |
| 5,608,148 | 3/1997 | John | 800/205 |

FOREIGN PATENT DOCUMENTS

| | | |
|---|---|---|
| 0 400 553 | 5/1990 | European Pat. Off. . |
| 486233 | 5/1992 | European Pat. Off. . |
| 92/06205 | 4/1992 | WIPO . |
| WO92/15675 | 9/1992 | WIPO . |
| WO95/25555 | 9/1995 | WIPO . |

OTHER PUBLICATIONS

Bidney et al. Plant Molecular Biology 1992.vol.18:301–313.
Potrykus I. Annu. Rev. Plant Physiol. Plant Mol. Biol. 1991. vol. 42: 205–225.
Bayley et al., "Engineering 2,4–D resistance into cotton," *Theor. Appl. Genet.* 83 (1992) pp. 645–649.
Beachy et al., "Coat Protein–Mediated Resistance Against Virus Infection," *Annu. Rev. Phytopathol.* 28 (1990) pp. 451–474.
Christou et al., "Stable transformation of soybean by electroporation and root formation from transformed callus," *Proc. Natl. Acad. Sci. USA* 84 (1987) pp. 3962–3966.
Comai et al., "Expression in plants of a mutant aroA gene from *Salmonella typhimurium* confers tolerence to glyphosate," *Nature* 317 (1985) pp. 741–744.

De Block et al., "Expression of foreign genes in regenerated plants and in their progeny," *The EMBO J.* 3 (1984) pp. 1681–1689.
Deshayes et al., "Liposome–mediated transformation of tobacco mesophyll protoplasts by an *Escherichia coli* plasmid," *The EMBO J* 4 (1985) pp. 2731–2737.
Feldmann et al., "*Agrobacterium*–mediated transformation of germinating seeds of *Arabidopsis thaliana:* A non–tissue culture approach," *Mol. Gen. Genet.* 208 (1987) pp. 1–9.
Finer et al., "Transformation of cotton (*Gossypium hirsutum* L.) via particle bombardment," *Plant Cell Reports* 8 (1990) pp. 586–589.
Fraley, et al., "Expression of bacterial genes in plant cells," *Proc. Natl. Acad. Sci. USA* 80 (1983) pp. 4803–4807.
Goldman et al., "Transformation of *Zea Mays* By *Agrobacterium Tumefaciens:* Evidence for Stable Genetic Alterations," *J. Cell. Biochem.* Feb. 1987, Supplement 11B, F202, p. 26.
Gordon–Kamm et al., "Transformation of Maize Cells and Regeneration of Fertile Transgenic Plants," *The Plant Cell* 2 (1990) pp. 603–618.
Hammock et al., "Expression and effects of the juvenile hormone esterase in a baculovirus vector," *Nature* 344 (Mar. 1990) pp. 458–461.
Horsch et al., "A Simple and General Method for Transferring Genes into Plants," *Science* 227 (Mar. 1985) pp. 1229–1231.
Jefferson, "Assaying Chimeric Genes in Plants: The GUS Gene Fusion System," *Plant Molecular Biology Reporter* 5 (1987) pp. 387–405.
Kado, "Molecular Mechanisms of Crown Gall Tumorigenesis," *Critical Reviews in Plant Sciences* 10 (1991) pp. 1–32.
Klein et al., "Transformation of Microbes, Plants and Animals by Particle Bombardment," *Bio/Technology* 10 (Mar. 1992) pp. 286–291.
Knutzon et al., "Modification of Brassica seed oil by antisense expression of a stearoyl–acyl carrier protein desaturase gene," *Proc. Natl. Acad. Sci. USA* 89 (Apr. 1992) pp. 2624–2628.

(List continued on next page.)

Primary Examiner—Douglas W. Robinson
Assistant Examiner—Ousama Zaghmout
Attorney, Agent, or Firm—Burns, Doane, Swecker & Mathis, L.L.P.

[57] ABSTRACT

The present invention relates to a method for producing a transgenic plant in which a transforming agent such as a recombinant Agrobacterium or an isolated DNA molecule capable of conferring a desired phenotypic trait is injected into plant tissues using a needleless injection device. A preferred embodiment of the method provides the precise delivery of the transforming agent to floral tissues of a plant, allowing the direct insertion of the DNA of the transforming agent into germline cells of the plant that develop into seeds. This embodiment provides a more efficient method of transformation and subsequent regeneration of a transgenic plant.

18 Claims, 4 Drawing Sheets

OTHER PUBLICATIONS

Chlan, C.A. et al, "A Procedure for Biolistic Transformation and Regeneration of Transgenic Cotton from Meristematic Tissue," *Pl. Molec. Biol. Rep.* 13(1):31–37 (1995).

Mumford, D.L., "A New Method of Mechanically Transmitting Curly Top Virus," *Phytopathology* 6k 2:1217–1218 (1972).

Koncz et al., "Expression and assembly of functional bacterial luciferase in plants," *Proc. Natl. Acad. Sci. USA* 84 (Jan. 1987) pp. 131–135.

McCabe et al., "Stable Transformation of Soybean (*Glycine Max*) By Particle Acceleration," *Bio/Technology* 6 (Aug. 1988) pp. 923–926.

McElroy et al., "Isolation of an Efficient Actin Promoter for Use in Rice Transformation," *The Plant Cell* 2 (Feb. 1990) pp. 163–171.

Moloney et al., "High efficiency transformation of *Brassica napus* using *Agrobacterium* vectors," *Plant Cell Reports* 8 (1989) pp. 238–242.

Murai et al., "Phaseolin Gene from Bean Is Expressed After Transfer to Sunflower Via Tumor–Inducing Plasmid Vectors," *Science* 222 (1983) pp. 476–482.

Odell et al., "Identification of DNA sequences required for activity of the cauliflower mosaic virus 35S promoter," *Nature* 313 (Feb. 1985) pp. 810–812.

Pang et al., "Expression of a gene encoding a scorpion insectotoxin peptide in yeast, bacteria and plants," *Gene* 116 (1992) pp. 165–172.

Sanford, "The biolistic process," *Tibtech* 6 (Dec. 1988) pp. 299–302.

Sanford, "Biolistic plant transformation," *Physiologia Plantarum* 79 (1990) pp. 206–209.

Schena et al., "A steroid–inducible gene expression system for plant cells," *Proc. Natl. Acad. Sci.*, (Dec. 1991) pp. 10421–10425.

Simpson et al., "Light–inducible and tissue–specific expression of a chimaeric gene under control of the 5'–flanking sequence of a pea chlorophyll a/b–binding protein gene," *The EMBO J.* 4 (1985) pp. 2723–2729.

Stalker et al., "Herbicide Resistance in Transgenic Plants Expressing a Bacterial Detoxification Gene," *Science* 242 (Oct. 1988) pp. 419–423.

Teeri et al., "Gene fusions to lacZ reveal new expression patterns of chimeric genes in transgenic plants," *The EMBO J.* 8 (1989) pp. 343–350.

Trolinder et al., "In vitro selection and regeneration of cotton resistant to high temperature stress," *Plant Cell Reports* 10 (1991) pp. 448–452.

Trolinder et al., "Genotype specificity of the somatic embryogenesis response in cotton," *Plant Cell Reports* 8 (1989) pp. 133–136.

van den Elzen et al., "A chimaeric hygromycin resistance gene as a selectable marker in plant cells," *Plant Molecular Biology* 5 (1985) pp. 299–302.

von Lintig et al., "Positive Regulators of Opine–Inducible Promoters in the Nopaline and Octopine Catabolism Regions of Ti Plasmids," *Molecular Plant–Microbe Interactions* 4 (1991) pp. 370–378.

Wang et al., "Whisker–Mediated Plant Transformation: An Alternative Technology," *In Vitro Cell. Dev. Biol.* 31 (Apr. 1995) pp. 101–104.

Ward et al., "Chemical regulation of transgene expression in plants," *Plant Molecular Biology* 22 (1993) pp. 36–366.

Hays, "Hunting Livestock Parasites with a Gene Gun," *Agricultural Research* (1997) pp. 10–11.

Floral Organs

Cotton Flower

IN PLANTA METHOD FOR THE PRODUCTION OF TRANSGENIC PLANTS

FIELD OF THE INVENTION

The present invention relates to a new method for the effective and reliable introduction of genes encoding desirable traits into the genome of a plant. The method utilizes a needle-free injection device to deliver DNA directly into cells of a plant tissue without causing excessive tissue damage. The method also provides for the direct delivery of the DNA to germline cells, allowing for the incorporation of the transforming DNA into the seeds of the plant.

BACKGROUND OF THE INVENTION

Current research in plant molecular biology is directed toward the development of improved plant varieties through the use of genetic engineering. Historically, improved plant varieties have been developed using classical genetic techniques to identify, preserve and crossbreed plants having desired traits. However, the genetic traits available to the classical breeder are limited to those that can be identified in the particular plant species the breeder is seeking to improve.

Advances in the application of the techniques of molecular biology to plants now allow for the introduction of new traits isolated from entirely different species into the plant of interest, particularly major crop plants such as cotton, maize, sorghum, soybeans, alfalfa, tobacco, and brassicas, such as rape. Traits that have been successfully transferred include insect resistance, herbicide resistance, stress tolerance, drought resistance, and disease resistance. Present day recombinant DNA technology has made it possible to identify new genes which effect the properties of plants and of products made from plants when they are transformed into new plant species. For example, a number of insect resistant varieties of cotton are presently being grown. Crop plants resistant to the herbicides Roundup, Buctril, and Liberty Link are now available, as are tomatoes which can be left on the vine longer than normal tomatoes, making mechanical harvesting of tomatoes easier and cheaper.

A variety of techniques have been used to introduce foreign genes into plant cells. However, most of these techniques are limited to use with plant tissues that must be regenerated into whole plants and require a period of time in tissue culture. Methods of regenerating whole plants from cells or tissues include, micropropagation of apical and lateral meristems, organogenesis, and somatic embryogenesis. Transformation of apical meristems, lateral meristems and organogenesis produce chimeric plants, i.e., plants which have the gene encoding the newly introduced trait in only a few cells, which may or may not be in the gene in germline tissue. Plants regenerated through somatic embryogenesis are rarely chimeric. Somatic embryos are usually derived from a single cell.

One common method used to introduce foreign genes into plant cells is transformation with Agrobacterium, a relatively benign natural plant pathogen. Agrobacterium actively mediates transformation events—the integration of a gene providing a desired phenotypic trait—as part of the natural process it utilizes when it infects a plant cell. Methods for transferring foreign genes into plant cells and the subsequent expression of the inserted genes in plants regenerated from transformed cells are well known in the prior art. See for example, M. De Block et al., *The EMBO Journal* (1984) 3:1681; Horsch et al. *Science* (1985) 227:1229; and C. L. Kado (*Crit. Rev. Plant. Sci.* (1991) 10:1.

The technique known as microprojectile bombardment has been used to successfully introduce genes encoding new genetic traits into a number of crop plants, including cotton, maize, tobacco, sunflowers, soybeans and certain vegetables. See for example, U.S. Pat. No. 4,945,050, issued to Sanford; Sanford et al., *Trends in Biotechnology* (1988) 6:299; Sanford et al., *Part. Sci. Technol.* (1988) 5:27; J. J. Finer and M. D. McMullen, *Plant Cell Reports* (1990) 8:586–589; and Gordon-Kamm, *The Plant Cell* (1990) 2:603). Transformation by microprojectile bombardment is less species and genotype specific than transformation with Agrobacterium, but the frequencies of stable transformation events achieved following bombardment can be quite low, partly due to the absence of a natural mechanism for mediating the integration of a DNA molecule or gene responsible for a desired phenotypic trait into the genomic DNA of a plant. Particle gun transformation of cotton for example, has been reported to produce no more than one clonal transgenic plant per 100–500 meristems targeted for transformation. Only 0.1 to 1% of these transformants were capable of transmitting foreign DNA to progeny. See WO 92/15675. Cells treated by particle bombardment must be regenerated into whole plants, which requires labor intensive, sterile tissue culture procedures and is generally genotype dependent in most crop plants, particularly so in cotton. Similar low transformation frequencies have been reported for other plant species as well.

The inability to control the site of wounding of a plant tissue and thus the site to which the transforming agent is delivered is a significant disadvantage of microprojectile bombardment. The inability to target germline tissues accounts in part for the low transformation efficiencies achieved by microprojectile bombardment. In addition, bombardment frequently results in the delivery of more than one copy of the transforming DNA or gene into the genome of the transformed plant cell, which can cause deleterious effects to other agronomically important traits of the regenerated, transformed plant. Fragmentation of the DNA to be inserted can also occur when bombardment is used as the transformation method, resulting in transgenic plants which carry only a portion of the gene that is being inserted.

Attempts to improve the efficiency of microprojectile bombardment have been described. For example, tissues which have been bombarded are subsequently treated with an Agrobacterium carrying the gene of interest, as described in EPA 0486 233. The high velocity impact of the dense microprojectile particles has been hypothesized to generate an array of microwounds, creating an environment particularly conducive to infection by the Agrobacterium. However, these procedures provide transformed plant cells which must still be regenerated into whole plants and the fertile, stably transformed plants must be selected from the total population of regenerated plants.

Organogenesis, the development of plantlets from specific plant structures such as leaf disks or root tips, has been used to regenerate plants following transformation. However, organogenesis frequently produces plants which have originated from a group of cells, not just a single cell, and results in a chimeric plant containing both transformed and non-transformed cells. If the desired trait is to be passed on to subsequent generations of the plant, the introduced DNA must be incorporated into the genetic material of germline cells of the regenerated plant. If a mixture of transformed and nontransformed cells are involved in the regeneration of a new plant, only a portion of its cells will contain the gene encoding the transferred characteristic. The regenerated plant will be chimeric, and its germline cells may not be transformed at all. Successful transformation of plants requires that germline cells of the plant be transformed in such a way that progeny of the plant inherit the inserted gene. Otherwise, the introduced trait will be lost from progeny of the transformed plantlet.

Somatic embryogenesis, the development of embryos from somatic tissue, has been the method of choice for regenerating plants from transformed tissue. Somatic embryogenesis is superior to organogenesis in that the resulting regenerated plant is not chimeric. Somatic embryos are derived from a single cell thus all cells in the embryo contain the introduced DNA. Unfortunately, somatic embryogenesis is highly genotype dependent in most crop plants.

Methods for in planta transformation have been attempted to circumvent the time and expense of existing transformation techniques. Feldman has shown that it is feasible to vacuum infiltrate the floral meristems of small plants, or in the case of Arabidopsis, the entire plant with Agrobacterium and obtain transgenic progeny. See K. A. Feldman et al., "Agrobacterium-Mediated Transformation of Germinating Seeds of *Arabidopsis thaliana*: A Non-Tissue Culture Approach," *Mol. Gen. Genet.* (1987) 308:1–9.) Unfortunately, this technique is not feasible for large crop plants such as cotton, maize and soybeans.

Efforts have been made to develop transformation methods that deliver naked DNA to the germinating pollen tube of a plant, and subsequently to the egg cell in the floral tissue. Although expression of the inserted foreign genes has been observed, the transformants have proven to be unstable in future generations. The selection of stable, transformed plants produced by such procedures is extremely difficult due to the magnitude of the selection work involved in identifying the few transformants among the large numbers of plants that must be screened. Unlike the selection of transformed cells and tissues, which can be carried out under laboratory conditions, selection of transformed plants germinated from seed requires growth of sufficient numbers of plants in a green house or in an open field to allow identification of transformants.

Direct injection of floral tissues with a transforming agent has been attempted using ordinary syringes having needles. Direct injection with a needle results in excessive tissue damage, and provides little control of placement of the transforming agent. While direct injection with a needle places the transforming DNA within the plant, it must still be taken up by individual cells and it must be incorporated into the plant's genome. Again, since transformation frequencies of these methods are expected to be extremely low, selection of transformed plants is difficult.

Therefore, there still exists a need for a procedure that will allow the delivery of a transforming agent or DNA to germline tissues such that the agent or DNA will be incorporated directly into the DNA of the cells in these tissues, particularly into the DNA of the egg cells of the plant. A method which effectively and directly targets germline tissues would greatly improve the frequency with which the transforming agent is inserted into the genomic DNA of the germline tissues of the plant and is thus passed on to the progeny of the transformed plant.

The present invention provides an improved method for delivering transforming agents to germline tissues such that the agent or DNA will be incorporated directly into the DNA of the cells in these tissues, particularly into the DNA of the egg cells of the plant. A method which effectively and directly targets germline tissues would greatly improve the frequency with which the transforming agent is inserted into the genomic DNA of the germline tissues of the plant and is thus passed on to the progeny of the transformed plant.

The present invention further provides an improved method for delivering transforming agents to plant tissues, which overcomes deficiencies of the prior art methods by providing for the precise injection of a transforming agent, without causing excessive injury to the injected tissues. The method is particularly useful for delivering a transforming agent to developing floral tissues of a plant prior to or during seed development. The transforming agent may be a genetically engineered or recombinant Agrobacterium carrying a gene capable of conferring a desired phenotypic trait, or even a naked DNA molecule capable of conferring the desired trait. The method uses a needleless-injection device that is capable of injecting a small high pressure stream of a solution through the many cell layers of plant tissue. In one preferred embodiment of the invention the transforming agent is delivered to a plant's floral tissues, thereby facilitating delivery of a transforming agent comprising a gene of interest into germline cells of the plant. The high pressure stream provided by the injection device insures that the Agrobacterium culture or the DNA solution penetrates the many cell layers of the plant floral tissue without causing massive tissue damage, such as that caused by direct injection with a syringe having a needle or by particle bombardment. One of skill in the art of plant molecular biology will understand that the method of the present invention can also be adapted for transformation of plant cells and tissues, including embryonic tissue culture cells, meristematic tissues and plant callus, which can be regenerated into whole plants. They will also recognize that the method can be adapted for introducing DNAs conferring phenotypic traits into plant tissues and cells to be used in transient transformation assays and in other assays used in plant research.

DETAILED DESCRIPTION OF THE INVENTION

Figure 1:
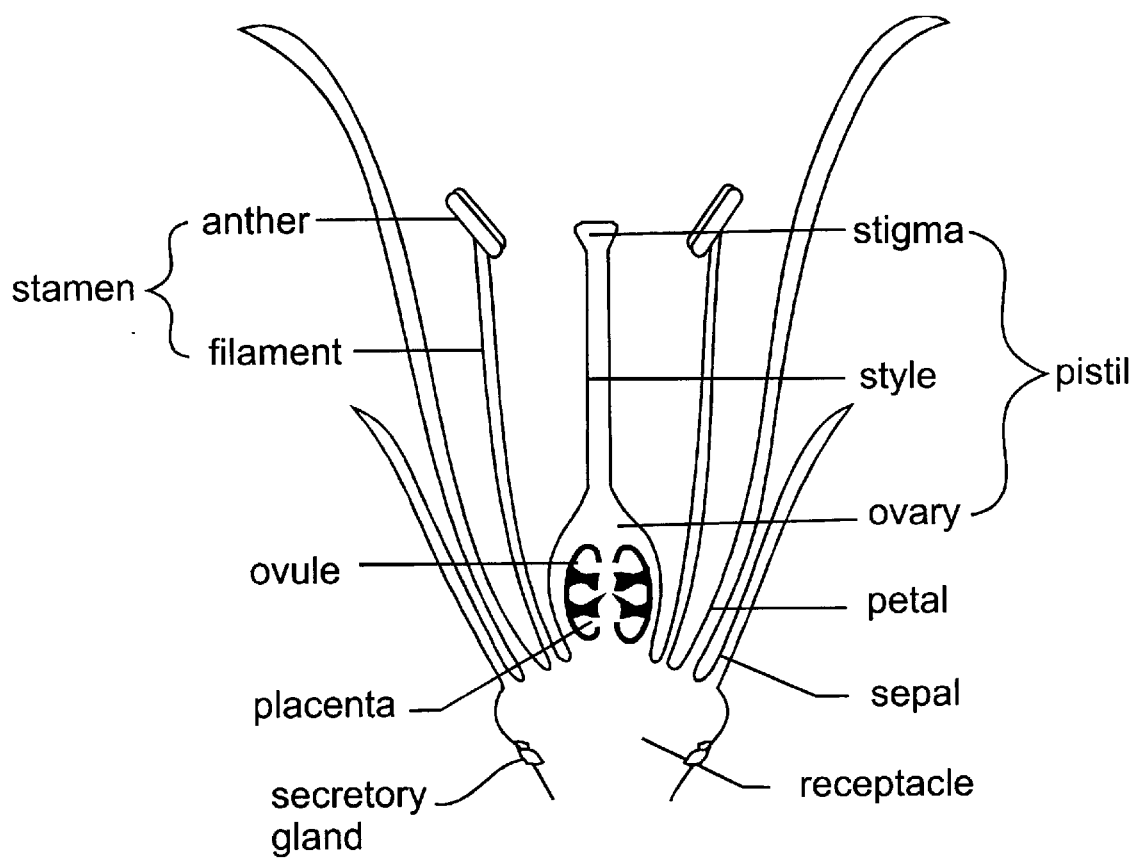
FIG. 1 is a diagram of floral tissues of a plant, indicating the reproductive organs to which the transforming agent may be directed.
Figure 2:
FIG. 2 is a diagram of the floral tissues of a cotton plant.

The present invention relates to a method for producing a transgenic plant, which can be used to transform any seed bearing plant species or asexually propagated plant species. The method provides for the introduction of a transforming agent into the genomic DNA of a plant cell or tissue, and comprises the injection of a transforming agent into a plant tissue or cell using a needleless injection device such as a hypodermic jet syringe. The transforming agent can be any suitable agent comprising a nucleic acid molecule capable of conferring a desired phenotypic trait to a plant, which can be introduced into a plant tissue using a needleless-injection device. Preferred transforming agents include a recombinant, or genetically engineered Agrobacterium and an isolated DNA molecule. The procedure maximizes the number of germline transformation events achieved from a single transformation procedure, so that the entire transformation process can be carried out on a manageable scale, producing large numbers of independent, transformed plants and plant cells.

The present invention provides a new method for producing transgenic plants which overcomes problems in prior art transformation methods. One of skill in the art of plant molecule biology will understand that the term "transgenic plant" means a new plant created by introducing an isolated DNA into the genome of the starting plant. The term "gene" means a nucleic acid molecule, which is usually a DNA molecule, but can also be an RNA molecule. The nucleic acid molecule may be a DNA fragment which encodes a protein which is expressed by the plant cell into which it has been introduced, thereby providing the desired phenotypic trait to the plant comprised of the transformed cells. Expression of the protein in a plant cell is responsible for the altered characteristics of the cell, and consequently the characteristics of a plant comprised of the transformed cells.

Introduction of a transforming agent providing a trait which one desires to introduce into a plant with a needleless-injection device provides one of skill in this art with the ability to control the site at which a transforming agent is delivered to the plant. In one preferred embodiment of the present invention the injection device is used to deliver the transforming agent to the floral tissues of a plant, particularly the placental area of the ovary, where the agent is able to proceed to the ovule via the vascular system of the plant tissue and enter the embryo sac. The transforming agent may enter the egg through the plasma membrane, through the discontinuous wall at the chalazal portion of the egg, or through the micropylar pore prior to fertilization. Unlike prior art methods of transformation used for plants, such as microprojectile bombardment which yield transgenic plants that are generally chimeric, the present method can theoretically produce a number of transgenic plants equal to the number of seeds in the developing fruit of that plant. When the transformation is done at an early stage in seed development, each transformed plant germinating from a single seed will be entirely transgenic. That is, each cell of the plant will carry the introduced gene in each of its cells.

Plants and tissues used for transformation. The method of the present invention can be used to transform any species of plant, including monocots and dicots. The higher transformation frequencies achieved with the method overcome the difficulties associated with obtaining sufficient numbers of transformed plants to make screening feasible. Representative dicot plant species which may be transformed by the method of the present invention include cotton, soybeans, alfalfa, flax, tobacco, sunflowers, peanuts, fruits, such as strawberries and tomatoes, and vegetables such as peas, beans, squash, and peppers. Preferred dicots which can be used in the present invention include cotton, sunflower and pepper, particularly bell pepper. A preferred embodiment of the invention is use of the method for transformation of a cotton plant. Monocot species which may be transformed using the method include maize, sorghum, barley, oats, rye, wheat, and rice.

Any desired plant tissue, including floral tissues of intact plants, meristematic tissues, embryonic tissue culture cells, or callus tissue, can be transformed using the method of the present invention. A preferred embodiment of the present invention introduces a transforming agent into floral tissues of a plant to produce recombinant seeds which can be germinated into transformed plants.

FIG. 1 of the present application is a diagram of the floral tissues of a generalized plant. In a preferred embodiment of the invention the transforming agent is injected into the plant at the base of the ovary in the floral tissues. Prior to injection the plant tissues are prepared by pretreating the floral bracts of the plant with several drops of a commercial bloom set, such as GA3, to reduce abscission of the treated bloom and insure normal development of embryos. Alternatively, GA3 may be incorporated into the solution containing the transforming agent. The use of young, healthy plants for injections also aids in reducing abscission of treated floral tissues and in growth of transformed embryos.

Genes Used for Transformation. The transforming agent used in the present invention can be a foreign gene selected to introduce or confer a desired trait into the transformed plant. It will be understood by those of skill in the art of plant molecular biology that the foreign gene will be comprised of DNA, or in certain instances may be comprised of RNA, such as antisense RNA. The trait to be introduced may promote growth of the plant, provide disease resistance, provide a change in plant morphology or in quality of a plant product, or provide any other change which can be accomplished by genetic manipulation of the genome of the plant. DNA encoding the new trait to be inserted into the plant is generally in the form of a plasmid vector and is constructed using methodology known to those of skill in the art of plant molecular biology. Exemplary methods are described in *Current Protocols In Molecular Biology*, F. Ausubel et al. (eds.), Wiley Interscience (1990) and "Procedures for introducing foreign DNA into plants" in *Methods in Plant Molecular Biology and Biotechnology*, B. R. Glick, and J. E. Thompson, eds., CRC Press, Inc., Boca Raton, (1993).

The DNA to be expressed is flanked by suitable promoters known to function in plant cells, such as the 35S promoter from cauliflower mosaic virus (CaMV), described by Odell et al., *Nature* (1985) 313:810; or the nopaline or octopine synthetase promoters (NOS) from Agrobacterium, described by Vontling et al., *Mol. Plant-Microbe Interactions* (1991) 4:370; and M. de Block et al., *The EMBO Journal* (1984) 3:1681. Any promoter which functions in a plant can be used to express the gene encoding the desired trait, including inducible, tissuespecific, tissue-preferred or constitutive promoters. Other regulatory sequences such as transcription termination sequences, polyadenylation sequences, and intervening sequences, or introns, which provide enhanced levels of expression may also be included in the DNA construct or plasmid used for transformation. Depending upon the desired function of the gene, it may be desirable to include protein sequences which direct the secretion or intracellular compartmentalizations of the DNA to be expressed. Such sequences are well-known to those of skill in the art of plant molecular biology.

The plasmid may also contain a DNA sequence encoding a selectable marker gene or a screenable marker gene, which can be used to identify individual transformed plants. The marker may allow transformed plants to be identified by negative selection or by screening for a product encoded by a genetic marker. Suitable selectable markers include antibiotic and herbicide resistance genes such as the neomycin transferase gene (NPTII) described by Fraley et al., *Proc. Natl. Acad. Sci. U.S.A.* (1983) 80:4803 and by van den Elzen et al., *Plant Mol. Biol.* (1985) 5:299; the or the phosphinothricin acetyl transferase genes (pat and bar) described in U.S. Pat. Nos. 5,561,236 and 5,276,268. Markers which may be used to directly screen for transformed plants include the β-glucuronidase gene (GUS), the luciferase gene, the green fluorescence protein gene and the chloramphenicol acetyltransferase gene. R. G. Jefferson, *Plant Molecular Biology Reporter* (1987) 5:387; C. Koncz et al., *Proc. Natl. Acad. Sci.* (1987) 84:131; Teri et al., *EMBO J.* (1989) 8:343; and De Block et al., *EMBO J.* (1984) 3: 1681. Any gene encoding a selectable or screenable marker known to function in plant cells or plant tissues may be used in the method.

Plants are transformed with genes encoded by DNA or by RNA which confers resistance to pathogens, disease or to pests, or with genes which alter and/or improve plant growth properties or the quality of plant products. For example, a gene encoding the *Bacillus thuringiensis* crystal endotoxin protein may be introduced into a plant to provide resistance to insects. Expression of this endotoxin in cells of a plant makes the plant tissues toxic when ingested by certain insect pests, providing transformed plants that are resistant to harmful insect pests. For a review of the known Bt endotoxin genes, see Kelly, et al., "Pesticide-Producing Bacteria," in *Mol. Biol. and Biotech.*, Meyers, ed, VCH Publishers, New-York, pp. 668 (1995). Genes encoding Bt endotoxins are also disclosed in K. F. Chak et al., *Applied and Environmental Microbiology* (1994) 60:2415; and R. S. Bora et al., *Applied and Environmental Microbiology* (1994) 60:214.

The gene to be transferred can provide herbicide resistance to the transformed plant. For example, expression of the bacterial gene enolpyruvylshikimate 3-phosphate synthetase in cells of the plant confers resistance to the herbicide glyphosate to the transformed plants. A mutant AroA gene, which can be used to confer tolerance to glyphosate, is described by Comai et al., in *Nature* (1985) 317:741–744. Insertion of the bar or pat genes isolated from strains of Streptomyces confers resistance to the herbicide glufosinate to the transformed plants. One preferred embodiment of the method includes transformation of a plant with the 2,4-D resistance trait encoded by the monooxygenase gene tfdA from *Alcaligenes eutrophus* as described in C. Bayley et al., *Theoretical and Applied Genetics* (1992) 83:645–649.

In one embodiment, the present invention may be used to transform plants with DNA molecules encoding fiber-specific genes such as those disclosed in U.S. Pat. No. 5,597,718. Such genes or their equivalents may be used to alter the fiber characteristics of the cotton plant. A preferred embodiment is the transformation of a cotton plant with a transforming agent comprised of DNA molecules encoding a fiber-specific gene. A gene which enhances the yield of the desired plant product may also be used to transform plants. Such yield enhancement genes are known to those of skill in the relevant art.

The desired genes may be transformed into species of Agrobacterium which are then used for plant transformation. Convenient strains of Agrobacterium which are useful as vectors harbor a binary Ti plasmid system. These strains carry a first Ti plasmid having a virulence region and a second chimeric plasmid which contains the border regions of the T-DNA region of a wild-type Ti plasmid surrounding a chimeric gene construct which includes the foreign gene of interest. Agrobacterium strains which harbor cointegrate type Ti plasmids are also useful as vectors in the plant transformation methods of the present invention. Suitable binary and cointegrate Ti plasmids are well know to those of skill in the art of plant transformation. The binary system is preferred because the smaller plasmid, containing the T-DNA borders, can be constructed and manipulated in an alternative host such as *E. coli*, then reintroduced to Agrobacterium. Preferred species for use in the method of the present invention include *Agrobacterium tumefaciens* strains LB4404 and EHA105.

Alternatively, the foreign genes are injected as purified plasmid DNA. Purified DNA is prepared according to standard methods known to those of skill in the art of plant molecular biology. For example, plasmid DNA containing the gene encoding the trait of interest can be transformed into *E. coli*, and isolated from the cellular material by alkaline lysis of the recombinant cells, followed by precipitation of the DNA. The DNA can be purified by any standard technique, such as CsCl density gradient centrifugation. One convenient technique is provided by the BIO 101 RPM-1G DNA preparation kit available from BIO101, 1070 Joshua Way, Vista, Calif. 92083.

DNA Delivery Process. DNA or Agrobacterium is delivered in planta directly to developing floral or meristematic tissue with a needle-free hypodermic injection syringe. Any needle-free injection device can be used in the disclosed method provided that it can be adapted for the injection of small volumes of material in a precise manner. The preferred device is spring loaded to propel the sample through a small orifice at a pressure sufficient to penetrate the tissues of the plant to be transformed and to place the sample appropriately and precisely. A suitable delivery device will have an adjustable pressure mechanism, which allows for precise adjustment of the amount of sample to be injected. One needle-free hypodermic injection device suitable for use in method is the Vitajet, which is available from Vitajet Corporation, 27075 Cabot Road, Laguna Hills, Calif.

The amount of sample delivered by the hypodermic injection device is controlled by adjusting the size of the sample chamber. The Vitajet device can be adjusted to deliver from 2 units (20 $\mu$l) to 50 units (500 $\mu$l) of transforming agent. The sample size and angle of penetration determines the trajectory of the sample through the tissue. If the dosage and angle are properly selected, the sample will enter the vascular system and be deflected upward to follow the vascular traces and diffuse into nearby tissues. If the dosage is too high the sample will travel directly through the vascular system and exit the tissue on the opposite side of the entry site. For example, for a pin head square floral tissue of cotton, a 20 $\mu$l sample delivered to the base of the square and angled slightly downward will enter the floral bud, be deflected upward through the center of the developing ovary, traversing the sites of ovule attachment without destroying the developing ovules. With larger doses, the sample will exit the ovary at the apex, after having traveled directly through the entire placental transmitting tissue of the ovary.

To deliver the sample to the developing zygote one day after anthesis, 50 $\mu$ls can be delivered through the apex of the ovary. The sample travels through the center of the ovary and pools at the base of the connective tissue in the ovary. If the sample is delivered to the base of the ovary, a 5 $\mu$l sample will pool at the base of the connective tissue to which the ovules are attached and diffuse upward. A larger volume delivered to the base will be deflected upward and exit the apex of the ovary of the floral tissues of the plant to be transformed. To deliver the sample to the shoot terminal of a cotton plant, entry of the injected material is directed to the axial nearest the terminal. No more than 20 $\mu$l of DNA containing solution can be used for this tissue. Fifty $\mu$ls of sample will result in the sample exiting directly opposite the entry site without traveling through the base of the square and will result in the formation of scar tissue. Greater than 50 $\mu$ls of sample will dissect the terminal. The entry site heals rapidly and leaves no visible scar if the proper dosage and angle are maintained. The parameters for injection may vary for each tissue type used in the methods. Determination of the exact parameters needed for a particular tissue can easily by made by those observing the course of the injection transforming agent through the plant floral tissues.

It is desirable to use a device having a sample chamber which can handle small samples on the order of 1 to 20 μls. A mechanism which allows for making fine adjustments to the sample volume injected is also desirable, particularly when transforming plant species having floral tissues that are generally smaller than cotton or maize. A preferred device will have an adjustable orifice so that the area into which the transforming agent is injected could be increased or decreased depending on the tissue being injected.

A preferred embodiment of the hypodermic injection device will allow for the injection of several tissues before the sample chamber must be reloaded to allow for rapid injection of multiple plants tissues. For example, where it is desirable to make 25 injections of 10 μls, each injection could be performed after loading the chamber with slightly more than the 250 μls of transforming agent if the injector was driven by a piston having a constant source of pressure supplied by a small motorized compressor. Alternatively, the injection device could be fitted with a means for attaching a vial containing a volume of transforming agent sufficient to provide material for 10 to 50 injections. Each time the piston of the injection device was fired, a new dose of transforming agent would be automatically reloaded into the loading chamber due to the vacuum created by expulsion of the previous dose of agent.

Existing devices are quite cumbersome, in that they require the depression of a button on the end of the device to inject the sample. The necessity of applying thumb pressure while trying to hold the device steady with one hand and the tissue with the other limits the precision with which the injection target is located. A preferred embodiment of the device has a button which can be depressed with the forefinger, like a trigger, while the tissue is automatically held in place by an attachment that gently surrounds the tissue and holds it tightly against the orifice. Different orifices designed to match the contours of the tissue to be injected aid in further positioning the tissue so that the injection site is precisely targeted. One of skill in the art will understand that a device capable of injecting a suitable small volume of a liquid at sufficient pressure to penetrate to the center of floral tissues or stems in such a manner that the stream can be directed upward as it enters the central area of the flower can be adapted for use in the method of the present invention.

Development of Seed From Transformed Tissues. Following injection of the transforming agent, floral tissues are allowed to develop undisturbed and are inspected daily for abscission. The plants are pollinated and the fruit, which in the case of cotton is referred to as bolls, are allowed to fully mature. Once the fruit has matured, the seeds are collected from the fruit and sowed in soil. The germinated seedlings produced from these seed are F1 progeny of the plant used in the transformation. These progeny are tested for the presence of the selectable marker gene as well as the expression of the inserted gene of interest.

Nodes on the main stem of the plant may also be injected using the needle-free hypodermic injection device, by injecting the transforming agent directly into the node. The leaves at the node are then removed to cause an axillary bud to emerge from the transformed meristematic region of the injected node. This newly formed branch will produce transformed fruit when the transforming agent is incorporated into embryonic cells which develop into germline tissue. Alternatively, the stem may be cut off above the injected node to cause the transformed axillary bud to emerge and re-establish apical dominance. This procedure will yield a transformed chimeric plant. Fruit developed on the chimeric plant above the transformed node will be transgenic when the transforming agent is incorporated into the cells of germline tissues which develop into seeds.

Methods for Regenerating Transgenic Plants. Methods for regenerating transgenic plants from tissue cultures and embryonic tissues in cultures are known to those in the art of plant molecular biology. Cells of immature embryos and tissue callers may also be transformed by injecting a transforming agent into these tissues using a needleless hypodermic injection device. Methods for regenerating cotton plants from calli are described by N. L. Trolinder and X. Shang in *Plant Cell Reports* (1991) 10:448.

EXAMPLE I

Introduction of Recombinant Agrobacterium Containing the Neomycin Phosphotransferase and β-glucuronidase Genes into the Floral Tissues of Cotton.

Preparation of the transforming agent and the floral tissues of the plant to be transferred. Recombinant *Agrobacterium tumefaciens* strain LB4404 was used to introduce the selective marker gene neomycin transferase and the gene encoding β-glucuronidase into floral tissues of cotton. LB4404 carries plasmid pBI121, a 13.0 kilobase (Kb) plasmid which was derived from pBI101 and is commercially available from Clontech Laboratories Inc., Palo Alto, Calif. pBI121 contains an 800 basepair HindIII-BamHI fragment encoding the protein β-glucuronidase (GUS) cloned immediately downstream from the cauliflower mosaic virus promoter, and an 800 basepair PstI-Hind III fragment encoding neomycin transferase (NPTII) immediately downstream of the NOS promoter. The plasmid also contains a 300 bp NOS terminator sequence immediately downstream of the NPTII sequence. The stable introduction of pBI121 into a plant cell confers resistance to the antibiotic kanamycin to the cell, and provides significant levels of expression of the detectable enzyme GUS.

Cultures of *Agrobacterium tumefaciens* LB4404 were maintained according to established methods known to those of skill in the art. The recombinant plasmid was mobilized into the Agrobacterium using the triparental procedures described by Ditta et al., *Proc. Natl. Acad. Sci.* (1980) 77:7347. The night before the transformation was done, cultures were grown in the presence of acetosyringinone, an inducer of the vir gene function.

The subtending floral bracts of the cotton plant were prepared by placing several drops of GA3, a commercial bloom set, at a concentration of 100 micrograms (ug) per liter (l) on the inner surface of the subtending floral bracts. This pretreatment is not required; however it reduces abscission of the cell and assists in normal embryo development. The use of young, healthy plants grown during the spring and summer for transformation also helps reduce abscission and assure the health of transformed embryos.

Transfer of the genes encoding kanamycin resistance and β-glucuronidase into cotton floral tissues. A 1:10 dilution of an overnight culture of the nononcogenic *A. tumefacien* strain LB4404 was prepared using Murashige and Skoog's basal salts containing Gambourg's B5 vitamins, and 30 grams of glucose per liter at pH 5.8. (Murashige and Skoog, *Physiol. Plant* (1962) 15:474.) The diluted culture was injected into a sterile vial through a septum, the needle of the special loading device of a Vitajet needle-free hypodermic injection device was inserted into the septum of the vial, and the Vitajet is attached to the loading device. The desired number of μls of Agrobacterium solution was drawn into the sample chamber of the Vitajet and the loading device was removed.

The floral tissues of the plant selected for injection had developed to a stage where the floral bud measured approximately 6 mm from the tip of the bud to its base. At this early bud stage until one day post anthesis, the tissue was injected at the base of the ovary. Ovaries may also be injected at the manually flattened apex of the structure from one day post anthesis until immediately before the division of the egg cell which occur 1 to 5 days post anthesis, depending upon environmental growth conditions.

On the day of injection several drops of GA3 solution were placed on the inner side of the floral bract, after which one of the bracts was removed to expose the base of the ovary. The orifice of the injection device was place directly against the ovary base from the side and the diluted culture sample was injected into the tissue by pushing the injection button of the Vitajet. Care was taken to position the Vitajet nozzle and to hold it tightly against the tissue to insure that the small injection site was almost invisible and that no scar tissue formed.

The amount of diluted Agrobactertium cell culture injected varied with the developmental stage of the injected tissue. Floral tissues from pin head square stage up to one day post anthesis (–1DPA) were injected with 20 μls of the diluted culture. Tissues that have reached one day post anthesis in their development were injected with 50 μls of diluted culture and tissues which had reached the bloom stage (1DPA) were injected with 50 to 100 μls of diluted culture.

After tissues had reached the bloom stage (1DPA), ovaries were injected at their apex, as well as from the side of the base. To inject the apex, the sharp tip of the ovary or boll was gently removed at the place where the carpels meet to provide a flat surface. The orifice of the Vitajet injector was directly centered on the flat surface so that the Agrobacterium culture solution was injected into the center of the boll. Sufficient culture was injected so that it pooled in the placental area at the base of the boll.

Bolls –1DPA or older may also be injected through the secretory glands at the base of the boll. The orifice of the Vitajet is placed directly over the gland and the device is angled so that part of the solution will go up through the center of the base of the boll.

Following injection of the Agrobacterium, each boll was labeled with the date, dosage of the injection, the construct injected, the age of the boll and its position on the plant.

Floral tissues were allowed to continue their development undisturbed, and the injected bolls were checked daily for abscission. Multiple bolls were injected because it was expected that several of them would drop depending on the age of the tissue and environmental conditions in the greenhouse (cloudy days cause drop in cotton). Bolls were allowed to fully mature after pollination.

Seeds were harvested and tested for expression of the introduced gene. Seeds transformed using LB4404 were germinated in the presence the selectable marker, kanamycin. Only seedlings which had been stably transformed with the NPTII gene will have acquired the kanamycin resistance trait which allows them to grow lateral roots in the presence of 25 μg/l of kanamycin. Seeds were sterilized and placed in tubes containing 10 ml of sterile Stewart's Gel_ita Agar containing 25 μg/l of kanamycin. Seedlings which germinated and developed lateral roots were then transferred to soil in pots and reared in the greenhouse. Leaves taken from these plants were assayed for NPTII and GUS activity to confirm that the plants have incorporated the DNA encoding the genes encoding NPTII of GUS.

EXAMPLE II

Introduction of Recombinant Agrobacterium Containing the Neomycin Phosphotransferase and 2,4-dichlorophenoxyacetic Acid Genes into the Floral Tissues of Cotton.

Figure 3:
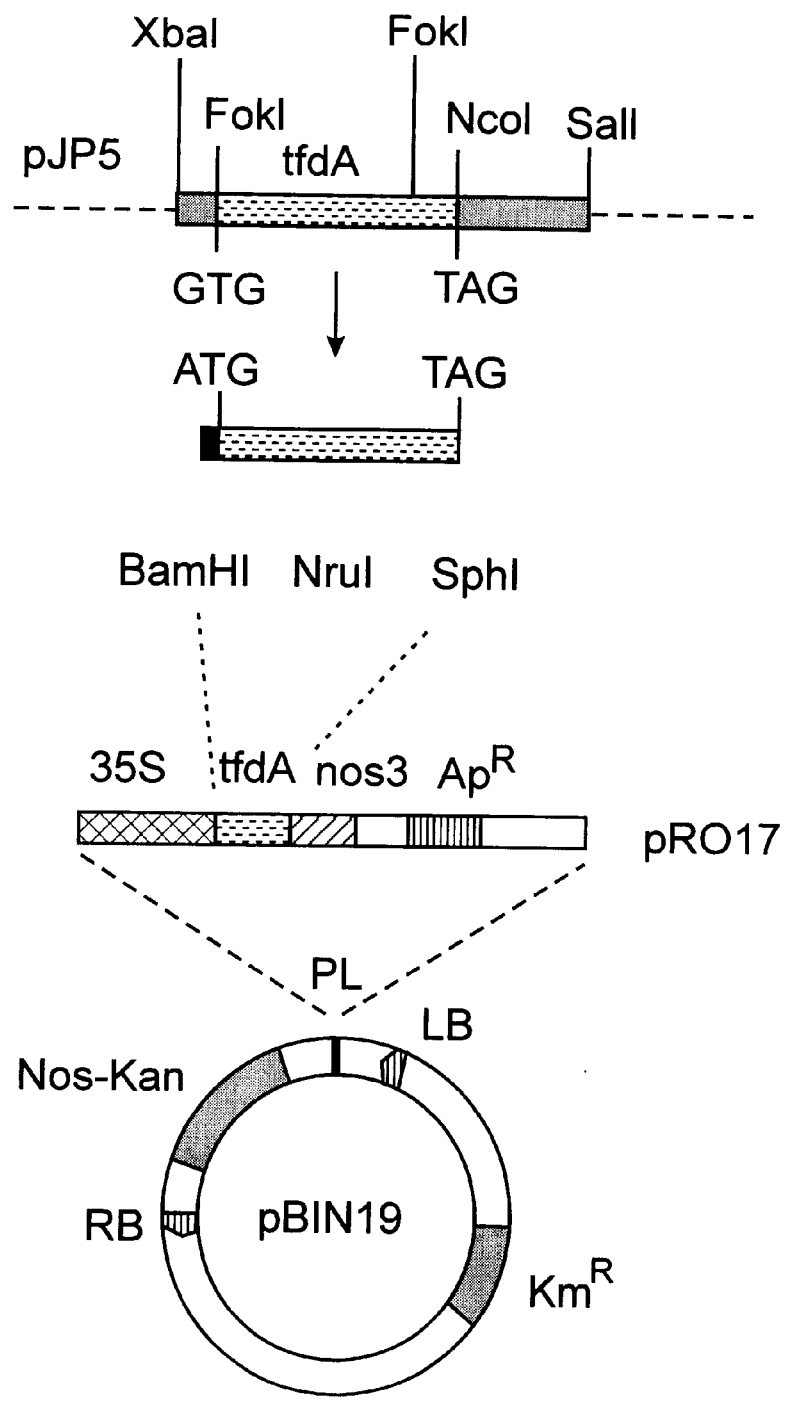
FIG. 3 is a map of pR017::pBIN19 indicating the site of insertion of pR017 into plasmid pBIN19.
Figure 4:
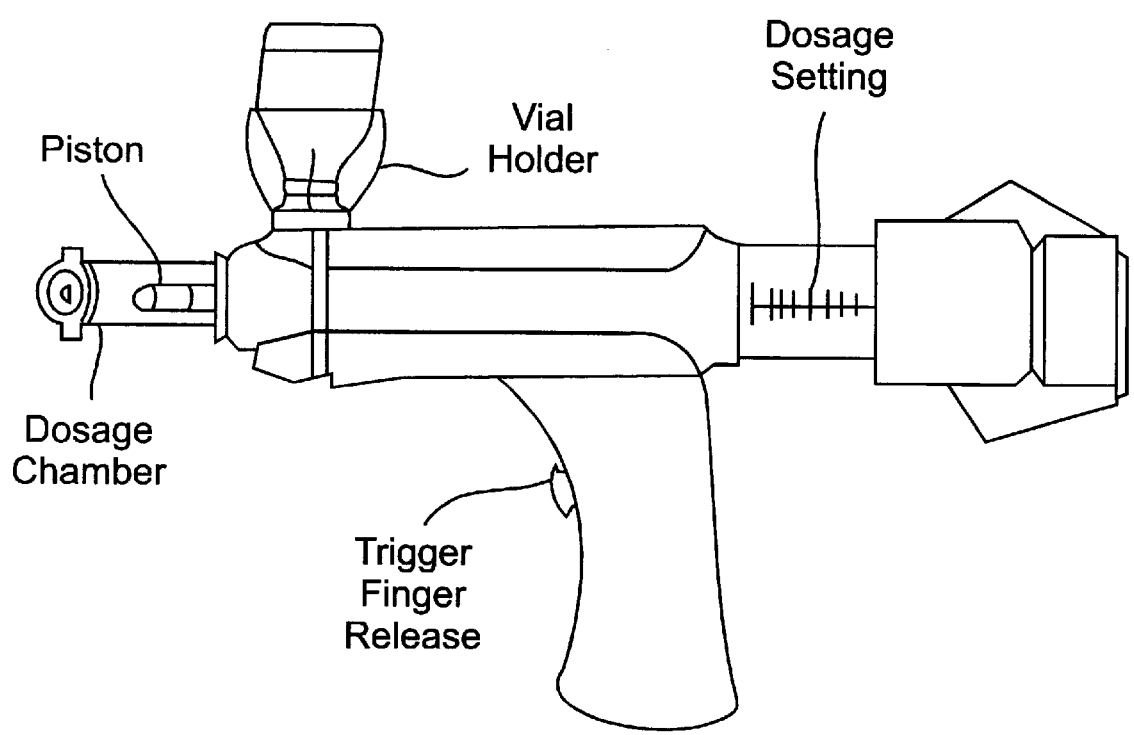
FIG. 4 is a diagram of a needle-free injection device having a trigger and a reservoir for providing injection of multiple samples without reloading the device.

Recombinant *Agrobacterium tumefaciens* strain EHA105 was used to introduce the selective marker gene encoding NPTII and the gene encoding into floral tissues of cotton. EHA105 carries plasmid pR017::pBIN19, which contains a 723 bp BamHI-SphI fragment containing the sequence of the tfdA gene cloned immediately downstream from the cauliflower mosaic virus promoter. FIG. 3 is a map of pR017::pBIN19, indicating the structure of the expression construct and the site at which it is inserted in pBIN19. See Bayley et al., *Theor. Appl. Genet.* (1992) 83:645 for a detailed description of the construction of pR017::pBIN19. The stable introduction of pR017::pBIN19, containing the tfda gene, into a plant cell confers resistance to the antibiotic kanamycin and to the herbicide 2,4-D.

Seeds developed from treated bolls were planted directly into soil. Germinated seedlings were sprayed with a 0.1× field level solution of 2,4-D when they reached the two leaf stage. At this stage of growth, treatment with 0.1× field level of 2,4-D causes profound strapping or deformity of the newly formed foliage. Plants which have been stably transformed with the tfdA gene are resistant to treatment with the herbicide and remain normal in appearance. Field level concentrations of 2,4-D kills all seedlings which do not carry the tfdA gene (0.1× severely straps the leaves of such seedlings) and are therefore not resistant to the herbicide. It is necessary to test with the lower level of 2,4-D to allow the observance of low expressing transformants since the objective is to identify transformation events and not necessarily plants with field level resistance as would be desirable for commercial purposes. Three sets of injections of floral tissues of cotton with strain EHA105 yielded 1162 progeny seed. These seeds were collected and treated with 0.1× field level of 2,4-D. Approximately 10% of the F1 progeny, 101 of the seedlings germinated from the 1162 seeds collected, were normal in appearance following herbicide treatment.

A method for producing a transformed plant by injecting a transforming agent into a plant issue using a needleless hypodermic injection device has been described in detailed herein and illustrated by way of specific examples. Those of skill in the relevant art of plant molecular biology will understand that the invention as described may be modified in various ways and used with various materials, and that the descriptions of the embodiments disclosed herein are not intended to limit the invention to the particular methods and materials of those embodiments. The invention, as defined in the appended claims, covers all modifications, equivalents, and alternatives which fall within the spirit and scope of the disclosed methods and compositions.

References cited to supplement, explain, or provide details of methodology, techniques and compositions employed in the invention, and to provide a background for understanding the disclosed invention are hereby incorporated by reference.

We claim:

1. A method for producing a transformed plant comprising, injecting Agrobacterium cells harboring a vector, comprising a nucleic acid molecule capable of conferring a desired phenotypic trait to a plant, into a plant floral or meristematic tissue using a needleless injection device, which can be adapted for the injection of small volumes of material in a precise manner without causing massive tissue damage.

2. The method of claim 1 wherein the plant tissue is a floral tissue of a plant.

3. The method of claim 1 wherein the plant tissue is an embryonic callus tissue.

4. The method of claim 1 wherein the plant tissue is a meristematic tissue.

5. The method of claim 1 wherein the plant is selected from the group consisting of cotton, soybean, alfalfa, flax, tobacco, sunflower, peanut, strawberry, tomato, pea, bean, squash, pepper, maize, sorghum, barley, oat, rye, wheat, rice, brassica and potato.

6. The method of claim 2 wherein the plant is selected from the group consisting of cotton, soybean, alfalfa, flax, tobacco, sunflower, peanut, strawberry, tomato, pea, bean, squash, pepper, maize, sorghum, barley, oat, rye, wheat, rice, brassica and potato.

7. The method of claim 3 wherein the plant is selected from the group consisting of cotton, soybean, alfalfa, flax, tobacco, sunflower, peanut, strawberry, tomato, pea, bean, squash, pepper, maize, sorghum, barley, oat, rye, wheat, rice, brassica and potato.

8. The method of claim 4 wherein the plant is selected from the group consisting of cotton, soybean, alfalfa, flax, tobacco, sunflower, peanut, strawberry, tomato, pea, bean, squash, pepper, maize, sorghum, barley, oat, rye, wheat, rice, brassica and potato.

9. The method of claim 5 wherein the plant is selected from the group consisting of cotton, soybean, alfalfa, flax, tobacco, sunflower, peanut, strawberry, tomato, pea, bean, squash, pepper, maize, sorghum, barley, oat, rye, wheat, rice, brassica and potato.

10. The method of claim 6 wherein the plant is selected from the group consisting of cotton, soybean, alfalfa, flax, tobacco, sunflower, peanut, strawberry, tomato, pea, bean, squash, pepper, maize, sorghum, barley, oat, rye, wheat, rice, brassica and potato.

11. The method of claim 1 wherein the transforming agent comprises a selectable marker gene.

12. The method of claim 13 wherein the selectable marker gene is selected from the group consisting of a neomycin transferase gene, a β-glucuronidase gene and a tfdA gene, the Pat gene and the bar gene.

13. The method of claim 1 wherein the transforming agent comprises an herbicide resistance gene.

14. The method of claim 1 wherein the transforming agent comprises an insect resistance gene.

15. The method of claim 1 wherein the transforming agent comprises a fiber-specific gene.

16. A method for producing a transgenic seed comprising injecting a Agrobacterium cells harboring a vector, comprising a gene capable of conferring a desired phenotypic trait, into the floral tissues of a plant before the division of the egg cell using a needleless-hypodermic injection device.

17. A method of producing a transgenic seed comprising injecting a recombinant Agrobacterium into the foloral tissues of a plant using a needleless-hypodermic injection device.

18. A method for producing a transgenic seed comprising injecting a Agrobacterium cells harboring a vector, comprising a gene capable of conferring a desired phenotypic trait, into the floral tissues of a plant before the division of the egg cell using a needleless-hypodermic injection device.

* * * * *

UNITED STATES PATENT AND TRADEMARK OFFICE
CERTIFICATE OF CORRECTION

PATENT NO. : 5,994,624

Page 1 of 2

DATED : November 30, 1997

INVENTOR(S) : Trolinder, et. al.

It is certified that error appears in the above-identified patent and that said Letters Patent is hereby corrected as shown below:

Column 13, lines 33-35, please delete "The method of claim 5 wherein the plant is selected from the group consisting of cotton, soybean, alfalfa, flax, tobacco, sunflower, peanut, strawberry, tomato, pea, bean,";

Column 14, lines 1-7, please delete "squash, pepper, maize, sorghum, barley, oat, rye, wheat, rice, brassica and potato.

10. The method of claim 6 wherein the plant is selected from the group consisting of cotton, soybean, alfalfa, flax, tobacco, sunflower, peanut, strawberry, tomato, pea, bean, squash, pepper, maize, sorghum, barley, oat, rye, wheat, rice, brassica and potato.";

Column 14, line 8, change "11" to --9--; and
change "transforming agent" to --Agrobacterium cells harboring a vector--;

Column 14, line 10, change "12" to --10--;

Column 14, line 14, change "13" to --11--; and
change "transforming agent" to --Agrobacterium cells harboring a vector--;

Column 14, line 16, change "14" to --12--; and
change "transforming agent" to --Agrobacterium cells harboring a vector--;

Column 14, line 18, change "15" to --13--; and
change "transforming agent" to --Agrobacterium cells harboring a vector--;

UNITED STATES PATENT AND TRADEMARK OFFICE
CERTIFICATE OF CORRECTION

PATENT NO. : 5,994,624
DATED : November 30, 1997
INVENTOR(S) : Trolinder, et. al.

It is certified that error appears in the above-identified patent and that said Letters Patent is hereby corrected as shown below:

Column 14, line 20-24, please change "16. A method for producing a transgenic seed comprising injecting a Agrobacterium cells harboring a vector, comprising a gene capable of conferring a desired phenotypic trait, into the floral tissues of a plant before the division of the egg cell using a needleless-hypodermic injection device." to --14. The method of claim 1 wherein the Agrobacterium cells harboring a vector comprises a yield enhancement gene.--;

Column 14, line 25, change "17" to --15--;

Column 14, line 26, change "foloral" to --floral--;

Column 14, line 29, change "18" to --16--;

Column 14, line 30, delete "a", first occurrence.

Signed and Sealed this

Twenty-fifth Day of July, 2000

Attest:

Q. TODD DICKINSON

Attesting Officer

Director of Patents and Trademarks